United States Patent [19]

Colquhoun

[11] Patent Number: 4,604,485

[45] Date of Patent: * Aug. 5, 1986

[54] CHEMICAL PROCESS

[75] Inventor: Howard M. Colquhoun, Knutsford, England

[73] Assignee: Imperial Chemical Industries PLC, London, England

[ * ] Notice: The portion of the term of this patent subsequent to Jul. 8, 2003 has been disclaimed.

[21] Appl. No.: 616,895

[22] Filed: Jun. 4, 1984

[30] Foreign Application Priority Data

Jun. 7, 1983 [GB] United Kingdom ............... 8315610

[51] Int. Cl.$^4$ ............................................. C07C 45/46
[52] U.S. Cl. .................... 568/319; 568/322; 560/66
[58] Field of Search .................... 560/66; 568/319, 322

[56] References Cited

U.S. PATENT DOCUMENTS

| 2,728,747 | 12/1955 | Aelony et al. | 560/66 |
| 2,763,691 | 9/1956 | Knowles | 568/319 |
| 3,073,866 | 1/1963 | Stanley | 568/322 |
| 3,160,665 | 12/1964 | Siegrist et al. | 568/319 |
| 3,548,005 | 12/1970 | Milionis et al. | 568/322 |
| 3,549,593 | 12/1970 | Takekoshi | 560/66 |
| 3,759,870 | 9/1973 | Economy et al. | 560/66 |
| 4,453,010 | 6/1984 | Staniland | 568/322 |
| 4,454,350 | 6/1984 | Desbois | 568/319 |

FOREIGN PATENT DOCUMENTS 0069598 1/1983 European Pat. Off. ............ 568/322

OTHER PUBLICATIONS

Stille, Condensation Monomers (1972) John Wiley & Sons, pp. 620–623.
Hill, Jo. Am. Chem. Soc., vol. 54, pp. 4105–4106 (1932).

Primary Examiner—James H. Reamer
Attorney, Agent, or Firm—Cushman, Darby & Cushman

[57] ABSTRACT

Preparation of para-substituted 4-hydroxybenzophenones by forming poly(4-oxybenzoyl) in situ and reacting it with an appropriately substituted aromatic compound. The poly(4-oxybenzoyl) can be formed from a precursor such as 4-hydroxybenzoic acid by reaction with an agent which removes water from the acid to form the polymer. The reaction with the appropriately substituted aromatic compound, for example fluorobenzone, is effected in the presence of a Lewis acid compound such as aluminum chloride.

18 Claims, No Drawings

CHEMICAL PROCESS

CHEMICAL PROCESS

This invention relates to a chemical process and more particularly to a method for the preparation of 4-hydroxybenzophenones.

A number of substituted diaryl ketones, for example 4-fluoro-4′-hydroxybenzophenone, are useful as precursors of poly(arylene ether ketones). Several methods have been proposed for the preparation of these diaryl ketones but none has proved to be entirely satisfactory.

Thus, it is known to make 4-fluoro-4′-hydroxybenzophenone by reacting phenol with 4-fluorobenzoic acid in anhydrous hydrogen fluoride with or without the addition of boron trifluoride. The reaction provides the desired product in high yield and good selectivity but has a number of disadvantages which make it unattractive as a basis for an industrial process.

First, 4-fluorobenzoic acid is a very costly starting material. Second, hydrogen fluoride, used as solvent/catalyst, is a very dangerous material requiring extremely careful and skillful handling. Third, water, formed as a by-product of the reaction produces, in conjunction with hydrogen fluoride, an extremely corrosive reaction mixture which severely limits the plant materials that may be employed, a situation which is further aggravated when boron trifluoride is present. Fourth, because of the water produced, the hydrogen fluoride has to be dehydrated before being recycled.

It is also known to make 4-fluoro-4′-hydroxybenzophenone by reacting 4-hydroxybenzoic acid with fluorobenzene in anhydrous hydrogen fluoride in presence of boron trifluoride. This method avoids using the expensive fluorobenzoic acid but still suffers from the disadvantages mentioned above associated with the use of hydrogen fluoride and with the formation of water as by-product.

Another known method of preparing hydroxybenzophenones is by the Fries rearrangement of phenyl benzoates in the presence of aluminium chloride or hydrogen fluoride. Again, the starting materials are expensive and the use of hydrogen fluoride causes the usual problems of handling. Unfortunately, when aluminium chloride is used in place of hydrogen fluoride, a mixture of the 2- and 4-hydroxy compounds is obtained and a separation process is required in order to obtain the desired 4-hydroxy compound having an adequate purity.

It has now been found that 4-hydroxybenzophenones may be prepared in excellent yield by making poly(4-oxybenzoyl) from a precursor thereof and reacting it with an appropriately substituted aromatic hydrocarbon in the presence of a Lewis acid. This method can be operated in conventional industrial plant as a "one-pot" process in which relatively cheap readily available starting materials are converted to the desired product in high yield. When used for the preparation of 4-fluoro-4′-hydroxybenzophenone, the desired product may be obtained in 98% selectivity with minimal production of unwanted isomers. Furthermore, the method may be operated using materials with which no unusual hazards are associated.

Thus, in accordance with the invention, a process is provided for the preparation of a 4-hydroxybenzophenone having the formula:

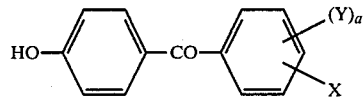

which process comprises polymerising a precursor of poly(4-oxybenzoyl) and reacting the poly(4-oxybenzoyl) so formed with an aromatic compound of the formula:

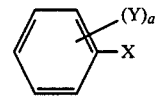

in the presence of an effective amount of a Lewis acid, wherein

X is hydrogen or a substituent which is not strongly electron attracting;

Y is a substituent which is not strongly electron attracting; and a is zero or an integer of 1 to 4; the remaining substituents being hydrogen atoms and the overall effect of X and the substituents Y is not sufficient to deactivate the aromatic compound to such an extent that substitution occurs only with difficulty.

The poly(4-oxybenzoyl) which is formed as an intermediate in the process of the present invention is a polyester having the general formula

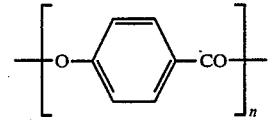

where n represents the degree of polymerisation. The value of n is at least 2 and may be as high as 1000. Depending on the procedure used, it is believed that the poly(4-oxybenzoyl) formed initially may be of low molecular weight, for example a dimer or trimer, and, in subsequent stages, this low molecular weight material may be converted into material of higher molecular weight. However, the process of the present invention is not restricted to the foregoing and includes all processes which involve the in situ formation of poly(4-oxybenzoyl) and its subsequent reaction with the specified aromatic compound.

A suitable precursor of poly(4-oxybenzoyl) for use in the process of the invention is 4-hydroxybenzoic acid. Using 4-hydroxybenzoic acid as the precursor, it is treated with an agent capable of converting the acid to the polymer. Such an agent may be one capable of removing water from the acid, thereby causing it to condense to form the polymer. The agent may be one which is capable of converting the carboxy group to a haloformyl, especially a chloroformyl, group. However, compounds containing groups such as a haloformyl group, that is compounds such as an acid halide, are not isolated in the process of the present invention and, under the reaction conditions used, are converted to the poly(4-oxybenzoyl). Agents capable of converting the acid to the polymer include carbonyl halides, for example phosgene, and particularly thionyl halides such as thionyl chloride. Other agents which may be ued include trifluoroacetic anhydride. It will be appreciated that the intermediate products obtained by treating 4-hydroxybenzoic acid with the agent which converts the acid to the polymer may be used as precursors for the production of poly(4-oxybenzoyl). However, such intermediate products are generally obtained from 4-hydroxybenzoic acid and may be difficult to isolate. Hence, it is preferred to use 4-hydroxybenzoic acid as the precursor for the polymer rather than to use any products which may be formed as an intermediate in obtaining the polymer from 4-hydroxybenzoic acid.

The treatment of 4-hydroxybenzoic acid to form poly(4-oxybenzoyl) is conveniently effected at a temperature in the range from 0° C. up to 100° C. The treatment may be effected in an inert solvent or in an excess of the aromatic compound which is to be reacted with the poly(4-oxybenzoyl). Suitable inert solvents include nitrobenzene, sulphur dioxide and 1,2,4-trichlorobenzene. It is preferred to use a slight excess of the agent used to convert 4-hydroxybenzoic acid into poly(4-oxybenzoyl), for example from 1.01 up to 1.20 moles of the agent for each mole of 4-hydroxybenzoic acid. The treatment with the acid may be carried out in the presence of a catalyst such as dimethylformamide. The temperature used is dependent on the agent used for this stage of the process. Thus, using thionyl chloride, a temperature of 60° C. to 90° C. is preferred whereas, using trifluoroacetic anhydride, the treatment may be effected at ambient temperature.

The reaction of the resulting poly(4-oxybenzoyl) with the aromatic compound may be effected in the presence of a Lewis acid, for example aluminium chloride or, less preferably, boron trifluoride. The reaction between the polyester and the aromatic compound is usually carried out at an elevated temperature, for example in the range 80° to 150° C. During the early stages of the reaction betwen the polyester and the aromatic compound, the thickness of the suspension has been observed to increase and the evolution of gases, such as hydrogen chloride, occurs. This is believed to indicate further polymerisation of the poly(4-oxybenzoyl) to material of higher molecular weight.

As stated herein, the aromatic compound used in the process of the invention has the general formula:

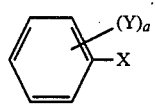

wherein X, Y and a are as defined. If the group X is a substituent group it may be an electron-donating substituent, for example alkyl, alkoxy or aryloxy, a substantially neutral substituent, for example aryl, or a mildly electron attracting substituent, for example halogen. In this connection, a strongly electron-attracting substituent is to be regarded as one which is more strongly electron-attracting than chlorine, for example cyano, nitro, alkylcarbonyl, alkoxycarbonyl or alkylsulphonyl. Persons skilled in the art will have no difficulty in identifying substituents which are not strongly electron-attracting when attached to an aromatic nucleus but a useful indication of the electron-donating or attracting properties of substituents may be obtained from their Hammett $\sigma$ constants which have been displayed and discussed by Clark and Perrin in Quarterly Reviews. Vol 18, 1964, pp 295-320. Substituents having a $\sigma$ constant for para-substitution of more than 0.4, tend to give a slow reaction and hence it is preferred to use substituents having a $\sigma$ constant of less than 0.4.

Thus, aromatic compounds which may be used in the process of the invention include benzene, alkylbenzenes for example toluene, alkoxybenzenes for example anisole, arylbenzenes for example biphenyl and 4-fluorobiphenyl, aryloxybenzones for example diphenyl ether and halogenobenzenes for example fluorobenzene, chlorobenzene and bromobenzene. In addition to the substituent X, the aromtic compound may carry one or more other substituents Y provided that the overall effect of all of the substituents (including X) is not deactivation of the aromatic compound to such an extent that reaction occurs only with difficulty. If the group Y is an even mildly electron-withdrawing group, for example halogen, it is preferred that there there are not more than two Y groups, and especially not more than one. The group Y may be the same as, or different from, the group X. Thus, other aromatic compounds which may be used include m-xylene, naphthalene and substituted naphthalenes free from strongly electron-attracting substituents. It is preferred that the aromatic compound is unsubstituted in the para-position relative to the X substituent.

The process of the invention may be conveniently performed using at least one mole of aromatic compound per mole of poly(4-oxybenzoyl) precursor. In fact, the aromatic compound may be used in sufficient excess to form the reaction medium but inert solvents may be employed for this purpose if desired. Alternatively, an excess quantity of the aromatic compound may be used together with an inert solvent. When employed as sole reaction medium, the aromatic compound is present at the start of the reaction sequence constituting the process of the invention. However, the aromatic compound may be present at the start of the reaction sequence even when an inert solvent is being used. Alternatively, the aromatic compound my be introduced into the reaction mixture after the polymerisation is complete.

Accordingly, one embodiment of the invention comprises polymerising a precursor of poly(4-oxybenzoyl) in the presence of a Lewis acid and an aromatic compound of the formula

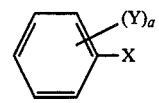

where X, Y and a are as defined.

A preferred embodiment of the invention comprises treating 4-hydroxybenzoic acid with an agent capable of converting the carboxy group to a haloformyl group and contacting the product with a Lewis acid in the presence of an aromatic compound of the formula:

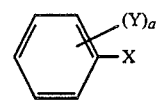

where X, Y and a are as defined.

A further preferred embodiment of the invention comprises treating a mixture of 4-hydroxybenzoic acid and an aromatic compound of the formula:

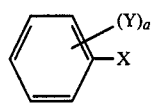

sequentially with (I) an agent capable of converting the carboxy group to a haloformyl group and (II) a Lewis acid, wherein X, Y and a are as defined.

The Lewis acid is preferably used in the process of the invention in an amount of at least one mole, preferably from 2 to 3 moles, per mole of poly(4-oxybenzoyl) precursor.

When the reaction has reached substantial completion, the 4-hydroxybenzophenone product may be isolated from the reaction mixture using conventional separation techniques, for example precipitation and filtration or distillation. Similarly, conventional purification methods may be employed when necessary, for example crystallisation and distillation.

The process of the invention has been found to be particularly effective for the preparation of 4-fluoro-4'-hydroxybenzophenone. This may be effected by treating a mixture of 4-hydroxybenzoic acid and fluorobenzene with, first, thionyl chloride and then aluminium chloride. In a preferred process, 4-hydroxybenzoic acid in an inert solvent is treated first with thionyl chloride, then with aluminium chloride and finally with fluorobenzene. The desired product is obtained in high yield (about 90%) and in very high purity accompanied by only small amounts, for example less than 4% by weight of 2-fluoro-4'-hydroxybenzophenone. The high purity of the product makes it suitable for use as a polyether ketone precursor with little further purification.

Products such as 4-fluoro-4'-hydroxybenzophenone may be used for the preparation of polyaryletherketones using a nucleophilic process, for example as described, inter alia, in British Pat. Nos. 1 078 234, 1 414 421, Canadian Pat. No. 847 963 and European Pat. No. 1879.

The invention is illustrated but not limited by the following Examples.

EXAMPLE ONE 4-hydroxybenzoic acid (27.6 g; 0.2 mol), thionyl chloride (25 g; 0.21 mol), and fluorobenzene (150 cm$^3$) were heated to reflux with 0.1 cm$^3$ of dimethyl formamide in a nitrogen atmosphere. After 1 hour, the mixture was cooled to room temperature, and anhydrous aluminium chloride (80 g; 0.6 mol) was added with stirring. The mixture was heated up to reflux temperature during which time hydrogen chloride was evolved and the mixture became thicker. After heating for a further 18 hours at reflux a solution was formed and this was cooled, poured into about 300 cm$^3$ of water at ambient temperature and the solid product was filtered off.

The solid product was washed repeatedly with water until the washings were acid free. The solid was then washed with hexane (about 200 cm$^3$). The solid was then dried in a vacuum oven at ambient temperature for 16 hours. The yield was 89% based on 4-hydroxybenzoic acid, and the product contained only traces (less than 0.5%) of hydroxybenzoic acid, together with less than 2% of 2-fluoro-4'-hydroxybenzophenone and more than 97% of 4-fluoro-4'-hydroxybenzophenone.

EXAMPLE TWO

A suspension of 4-hydroxybenzoic acid (69 g, 0.5 mol) in fluorobenzene (400 cm$^3$) was heated, in a nitrogen atmosphere, to 60° C. with stirring. Dimethylformamide (1 cm$^3$) and thionyl chloride (65 g, 0.55 mol) were added over a period of 30 minutes and the mixture was heated to 85° C. The suspension was stirred for two hours at 85° C. and then cooled to room temperature. The cold suspension was added, over a period of 30 minutes, to a stirred suspension of aluminium chloride (166 g, 1.25 mol) in fluorobenzene (100 cm$^3$) under nitrogen at 65° C. The temperature was raised to 85° C., during which time hydrogen chloride was evolved and the mixture became thicker. The mixture was stirred at 85° C. for 18 hours, at which time a solution had been formed. The solution was poured into one dm$^3$ of water at ambient temperature and the mixture was stirred. A solid separated. Unreacted fluorobenzene was recovered by distillation.

The solid product was filtered off, washed with water until acid free and dried to give a free flowing solid by passing a stream of air through the solid. The solid was dissolved in 500 cm$^3$ of 4% w/v aqueous sodium hydroxide solution and the solid was washed twice with 200 cm$^3$ of dichloromethane. The solution was acidified to a pH of about one by the addition of one molar hydrochloric acid. A precipitate was formed which was filtered off then washed repeatedly with water until the washings were acid free. The solid was then dried as in Example One.

The yield of 4-fluoro-4'-hydroxybenzophenone was 101 g (94% based on the 4-hydroxybenzoic acid).

EXAMPLE THREE

A procedure similar to that of Example Two was carried out, with the major exceptions that chlorobenzene was used rather than fluorobenzene and the aluminium chloride was added at elevated temperature.

More specifically, 27.6 g of 4-hydroxybenzoic acid, 150 cm$^3$ of chlorobenzene, 26 g of thionyl chloride and 0.3 cm$^3$ of dimethylformamide were used. After adding the thionyl chloride and dimethylformamide, the mixture was heated to 90° C. After stirring at 90° C. for one hour, 100 g of aluminium chloride were added in portions to keep the reaction under control. The mixture was then stirred at 90° C. for a further 20 hours. The solution formed was cooled and poured into one dm$^3$ of water and stirred. After 30 minutes the solid product was filtered off and purified by dissolving in aqueous sodium hydroxide, precipitating, washing and drying as in Example Two.

The yield of 4-chloro-4'-hydroxybenzophenone was 37 g (80% based on the 4-hydroxybenzoic acid). Chromatographic analysis revealed the presence of 3.5% by weight of 2-chloro-4'-hydroxybenzophenone.

EXAMPLE FOUR

A procedure similar to that of Example Two was carried out on a reduced scale with the exception that an inert solvent was used and fluorobenzene was not introduced until the last stage of the process.

4-Hydroxybenzoic acid (13.8 g, 0.1 mol), thionyl chloride (13 g, 0.11 mol), dimethylformamide (0.5 cm$^3$) and 1,2,4-trichlorobenzene (90 cm$^3$) were heated at 65° C. for 30 minutes and then at 90° C. for a further one hour. The mixture was cooled and added to a suspension of aluminium chloride (33 g, 0.25 mol) in a mixture of 1,2,4-trichlorobenzene (90 cm³) and fluorobenzene (20 cm³, 0.2 mol) at 60° C., whilst stirring. The mixture was heated to 120° C. and maintained at 120° C. for 8 hours. The mixture was cooled to 80° C. and poured into one dm³ of water at ambient temperature and the mixture was stirred. The solid was filtered off and purified as described in Example Two.

The yield of 4-fluoro-4'-hydroxybenzophenone was 18 g (83% based on the 4-hydroxybenzoic acid). Chromatographic analysis revealed the presence of about 3% by weight of 2-fluoro-4'-hydroxybenzophenone.

EXAMPLE FIVE

A procedure similar to that of Example Four was carried out using a different solvent and replacing fluorobenzene by diphenyl ether.

4-Hydroxybenzoic acid (27.6 g, 0.2 mol), thionyl chloride (26 g, 0.22 mol), dimethylformamide (0.2 cm³) and 1,2-dichlorobenzene (180 cm³) were heated at 65° C. for 4 hours. The mixture was cooled to 5° C. and diphenyl ether (68.1 g, 0.4 mol) and aluminium chloride (80 g, 0.6 mol) were added with stirring. A vigorous reaction ensued and when the gas evolution slowed, the reaction mixture was heated to 95° C. and stirred at this temperature for 8 hours. The solution obtained was cooled and poured into one dm³ of water at ambient temperature and the mixture was stirred. The aqueous phase was separated and rejected. The organic phase was extracted with 700 cm³ of 10% w/v sodium hydroxide. The aqueous phase was separated, filtered and acidified with concentrated hydrochloric acid. The precipiated solid was filtered off and washed with water until the washings were acid free. The solid was then dissolved in boiling ethanol, water was added to the boiling solution until a trace of precipitation was observed and the mixture was allowed to cool and the solid crystallised from the aqueous ethanol.

The yield of 4-hydroxy-4'-phenoxy-benzophenone was 39.6 g (68% based on the 4-hydroxybenzoic acid). The solid had a melting point of 145° C.

EXAMPLE SIX

A mixture of 4-hydroxybenzoic acid (27.6 g), 1,2,4-trichlorobenzene (200 cm³), dimethyl formamide (0.5 cm³) and thionyl chloride (26 g) was heated under nitrogen with stirring at 60° C. for 1 hour, and then at 90° C. for 1 hour. The reaction mixture was cooled to 80° C. and aluminium chloride (66 g) was added in portions over 10 minutes, and the slurry was stirred at 80° C. for a further 15 minutes. Fluorobenzene (58 g) was added, and the mixture was heated to 120° C. under fluorobenzene reflux. After 8 hours at this temperature the mixture was cooled to 70° C. and hydrolysed by addition of water (250 cm³), the temperature being maintained below 100° C. by external cooling. Excess fluorobenzene was recovered by distillation at 100° C. By GLC analysis, the distillate was found to consist of 89.6% of fluorobenzene, together with 9.4% of trichlorobenzene and 1% of chlorobenzene.

The hydrolysed reaction mixture was cooled to ambient temperature and stirred for 3 hours. The solid product was filtered off, washed with trichlorobenzene (100 cm³), then washed until acid free with water, and dried under vacuum. It was purified by dissolving in and precipitating from aqueous sodium hyroxide as in Example Two to give 34.3 g of 4-fluoro-4'-hydroxybenzophenone (79% based on the 4-hydroxybenzoic acid).

EXAMPLE SEVEN

In this example the 4-fluoro-4'-hydroxybenzophenone was polymerised. The procedure of Example Two was repeated and the product obtained was purified as follows.

A sample of 4-fluoro-4'-hydroxybenzophenone (67.8 g) containing 1.2% wt of the 2 fluoro-4'hydroxy isomer was dissolved in 324 cm³ of molar aqueous sodium hyroxide solution. Molar aqueous hydrochloric acid was added dropwise until the pH had fallen to 9.5. The precipiate was filtered off, washed with water (300 cm³) and dried under vacuum. The yield was 63.1 g (93% recovery) and the level of 2-fluoro-4'-hydroxy isomer had fallen to 0.5%.

The foregoing procedure was repeated on the recovered material, giving 59.9 g of product containing 0.2% of the 2-fluoro-4'-hydroxy isomer. This material was recrystallised from toluene (30 cm³ for each gramme of solid) to give 53.9 g of product containing 0.1% of the 2-fluoro-4'-hydroxy isomer.

A sample of the purified 4-fluoro-4'-hydroxybenzophenone (43.24 g, 0.2 mole) was polymerised using a mixture of sodium carbonate (10.56 g, 0.1 mole), and potassium carbonate (0.28 g, 0.002 mole) in diphenyl sulphone (93 g). The reaction mixture was placed in a 3-necked glass reaction flask under nitrogen and the flask was placed in a bath of silicone oil at 175° C. After 45 minutes, the temperature of the bath was raised slowly and after a further 40 minutes a temperature of 225° C. was attained in the reaction flask. The flask was maintained at 225° C. for 20 minutes while effervescence occured. The temperature was then raised to 260° C. over a period of 55 minutes. At this stage it was noted that polymer was being precipitated nd the temperature was raised to 300° C. over 30 minutes and then to 335° C. over a further 25 minutes, at which stage the reaction mixture was liquid, but viscous. The mixture was maintained at about 335° C. for a further 35 minutes and was then cooled.

The solid reaction product was then milled to pass through a 850 micrometer sieve. Diphenylsulphone and inorganic salts were removed by washing successively with acetone and water. The polymer was dried at 120° C. in an air oven.

The poly(phenylene ether ketone) had a melt viscosity of 0.31 KNs/m², measured at 400° C. and a shear rate of 1000 sec⁻¹. The polymer could be compression moulded at 400° C. into tough film.

I claim:

1. A process for the preparation of a 4-hydroxybenzophenone having the formula

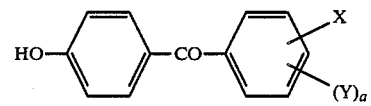

which comprises polymerising a precursor of poly(4-oxybenzoyl) and reacting in situ the poly(4-oxybenzoyl) so formed with an aromatic compound of the formula

in the presence of an effective amount of a Lewis acid wherein

X represents hydrogen or a substituent that is not strongly electron-attracting;

Y is a substituent which is not strongly electron attracting, and a is zero or an integer of 1 to 4;

the remaining substituents being hydrogen atoms and the overall effect of X and the substituents Y is not sufficient to deactivate the aromatic compound to such an extent that substitution occurs only with difficulty.

2. The process of claim 1 wherein the precursor of poly(4-oxybenzoyl) is 4-hydroxybenzoic acid which is treated with an agent capable of removing water from the acid to form poly(4-oxybenzoyl).

3. The process of claim 2 wherein 4-hydroxybenzoic acid is treated with an agent which is a carbonyl halide, a thionyl halide or trifluoroacetic anhydride.

4. The process of claim 2 wherein 4-hydroxybenzoic acid is treated with the agent capable of removing water from the acid at a temperature in the range 0° to 100° C.

5. The process of claim 1 wherein the reaction between the poly(4-oxybenzoyl) and the aromatic compound is carried out at 80° to 150° C.

6. The process of claim 1 wherein, in the aromatic compound, X is an alkyl, an alkoxy, an aryl, or an aryloxy group or a halogen atom.

7. The process of claim 1 which is effected in an inert solvent, an excess of the aromatic compound or a mixture of both an inert solvent and an excess of the aromatic compound.

8. The process of claim 1 wherein a mixture of 4-hydroxybenzoic acid and the aromatic compound is treated sequentially with (I) an agent capable of converting the carboxy group to a haloformyl group and (II) a Lewis Acid.

9. The process of claim 1 wherein the Lewis acid is aluminium chloride or boron trifluoride.

10. The process of claim 1 wherein the Lewis acid is used in an amount of at least one mole per mole of poly(4-oxybenzoyl) precursor.

11. The process of claim 1 for the production of 4-fluoro-4'-hydroxybenzophenone wherein a mixture of 4-hydroxybenzoic acid and fluorobenzene is treated with, first, thionyl chloride and then aluminium chloride.

12. The process of claim 1 for the production of 4-fluoro-4'-hydroxybenzophenone wherein a mixture of 4-hydroxybenzoic acid and an inert solvent is treated first with thionyl chloride, then with aluminium chloride and finally with fluorobenzene.

13. A process for the production of a poly(arylether ketone) by the nucleophilic polymerization of a 4-halo-4'-hydroxy-benzophenone wherein the 4-halo-4'-hydroxybenzophenone is the product of the process of claim 1.

14. A process for the preparation of 4-hydroxybenzophenone having the formula

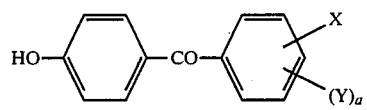

which comprises polymerising at a temperature in the range 0° C. to 100° C. a material which is a precursor of poly(4-oxybenzoyl) and is selected from 4-hydroxybenzoic acid and derivatives thereof, and reacting, in situ, the poly(4-oxybenzoyl) so formed with an aromatic compound of the formula

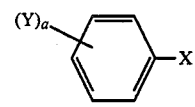

in the presence of an effective amount of a Lewis acid wherein

X represents hydrogen or a substituent that is not strongly electron-attracting;

Y is a substituent which is not strongly electron-attracting and a is zero or an integer of 1 to 4;

the remaining substituents being hydrogen atoms and the overall effect of X and the substituents Y is not sufficient to deacativate the aromatic compound to such an extent that the substitution occurs only with difficulty and the aggregate of Hammett $\sigma$ constants of X and the substituents Y is less than 0.4.

15. The process of claim 14 wherein 4-hydroxybenzoic acid is treated with an agent which is a carbonyl halide, a thionyl halide or trifluoroacetic anhydride.

16. The process of claim 14 wherein the Lewis acid is aluminium chloride or boron trifluoride.

17. A process for the production of 4-fluoro-4'hydroxybenzophenone wherein a mixture of 4-hydroxybenzoic acid and fluorobenzene is treated with, first, thionyl chloride at a temperature in the range 0° C. to 100° C. and the product mixture is reacted at a temperature of 80° C. to 150° C. in the presence of aluminium chloride.

18. A process for the production of 4-fluoro-4'hydroxybenzophenone wherein a mixture of 4-hydroxybenzoic acid and an inert solvent is treated first with a thionyl chloride at a temperature in the range 0° C. to 100° C., aluminium chloride and fluorobenzene are added to the product mixture which is heated to a temperature in the range 80° C. to 150° C.

* * * * *